United States Patent
Honda et al.

(10) Patent No.: US 7,670,610 B2
(45) Date of Patent: Mar. 2, 2010

(54) RECOMBINANT BCG VACCINE

(75) Inventors: Mitsuo Honda, Tokyo (JP); Kazuhiro Matsuo, Kanagawa (JP); Masaru Kanekiyo, Tokyo (JP); Duanthanorm Promkhatkaew, Muang Nonthaburi (TH)

(73) Assignee: Department of Medical Sciences-Ministry of Public Health of Thailand, Muang Nonthaburi (TH)

( * ) Notice: Subject to any disclaimer, the term of this patent is extended or adjusted under 35 U.S.C. 154(b) by 0 days.

(21) Appl. No.: 12/230,847

(22) Filed: Sep. 5, 2008

(65) Prior Publication Data
US 2009/0060954 A1 Mar. 5, 2009

Related U.S. Application Data

(62) Division of application No. 10/524,586, filed as application No. PCT/JP03/10303 on Aug. 13, 2003.

(30) Foreign Application Priority Data

Aug. 16, 2002 (JP) ............................. 2002-237610

(51) Int. Cl.
*A61K 39/02* (2006.01)
*A61K 39/04* (2006.01)
(52) U.S. Cl. .................. 424/248.1; 424/234.1; 435/41; 435/243; 435/440; 435/471
(58) Field of Classification Search ............. 424/234.1, 424/248.1; 435/41, 243, 440, 471
See application file for complete search history.

(56) References Cited

U.S. PATENT DOCUMENTS 5,504,005 A * 4/1996 Bloom

FOREIGN PATENT DOCUMENTS

| EP | 400973 | * | 12/1990 |
| WO | 90/00594 | * | 1/1990 |
| WO | 90/15873 | * | 12/1990 |
| WO | 92/01783 | * | 2/1992 |

OTHER PUBLICATIONS

International Search Report issued Dec. 9, 2003 in the International (PCT) Application No. PCT/JP03/10303.*
R. Yamaguchi et al., "Cloning and Characterization of the Gene for Immunogenic Protein MPB64 of *Mycobacterium bovis* BCG", Infection and Immunity, vol. 57, No. 1, pp. 283-288, 1989.*
S. Andersson et al., "Codon usage in the Mycobacterium tuberculosis Complex", Microbiology, vol. 142, No. 4, pp. 915-925, Apr. 1996.*
Edited by the Japanese Biochemical Society, "Shin Seikagaku Jikken Koza, vol. 1, Tanpakushitsu VII-Tanpakushitsu Kogaku-", Tokyo Kagaku Dojin, pp. 314-315, Feb. 15, 1993.*
W. R. Jacobs, Jr. et al., "Introduction of foreign DNA into mycobacteria using a shuttle plasmid", Nature, vol. 327, No. 6122, pp. 532-535, Jun. 11, 1987.*
L. Deml et al., "Multiple Effects of Codon Usage Optimization on Expression and Immunogenicity of DNA Candidate and Vaccines Encoding the Human Immunodeficiency Virus Type I Gag Protein", Journal of Virology, vol. 75, No. 22, pp. 10991-11001, Nov. 2001.*
D. L. Narum et al., "Codon Optimization of Gene Fragments Encoding *Plasmodium falciparum* Merzoite Proteins Enhances DNA Vaccine Protein Expression and Immunogenicity in Mice", Infection and Immunity, vol. 69, No. 12, pp. 7250-7253, Dec. 2001.*
M. Uchijima et al., "Optimization of Codon Usage of Plasmid DNA Vaccine is Required for the Effective MHC Class I-Restricted T Cell Responses against an Intracellular Bacterium", The Journal of Immunoolgy, vol. 161, pp. 5594-5599, 1998.*
K. Matsuo et al., "Cloning and Expression of the *Mycobacterium bovis* BCG Gene for Extracellular α Antigen", Journal of Bacteriology, vol. 170, No. 9, Sep. 1988, pp. 3847-3854.*

* cited by examiner

*Primary Examiner*—Rodney P. Swartz
(74) *Attorney, Agent, or Firm*—Wenderoth, Lind & Ponack, L.L.P.

(57) ABSTRACT

A recombinant BCG vaccine being transformed with an expression vector that has a polynucleotide encoding a foreign antigenic protein, wherein the polynucleotide is a modified one in which the third position of each codon is substituted with G or C without a change of an amino acid. This recombinant BCG vaccine has an excellent expression rate of antigenic protein and, as a result, capable of inducing a sufficient immune response against target infectious disease, cancer, or the like at the same dose as that of the typical BCG vaccine.

2 Claims, 5 Drawing Sheets

Fig. 1

Fig. 2
A
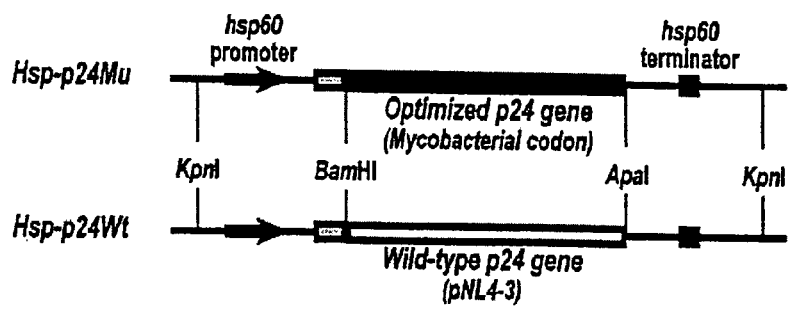
B
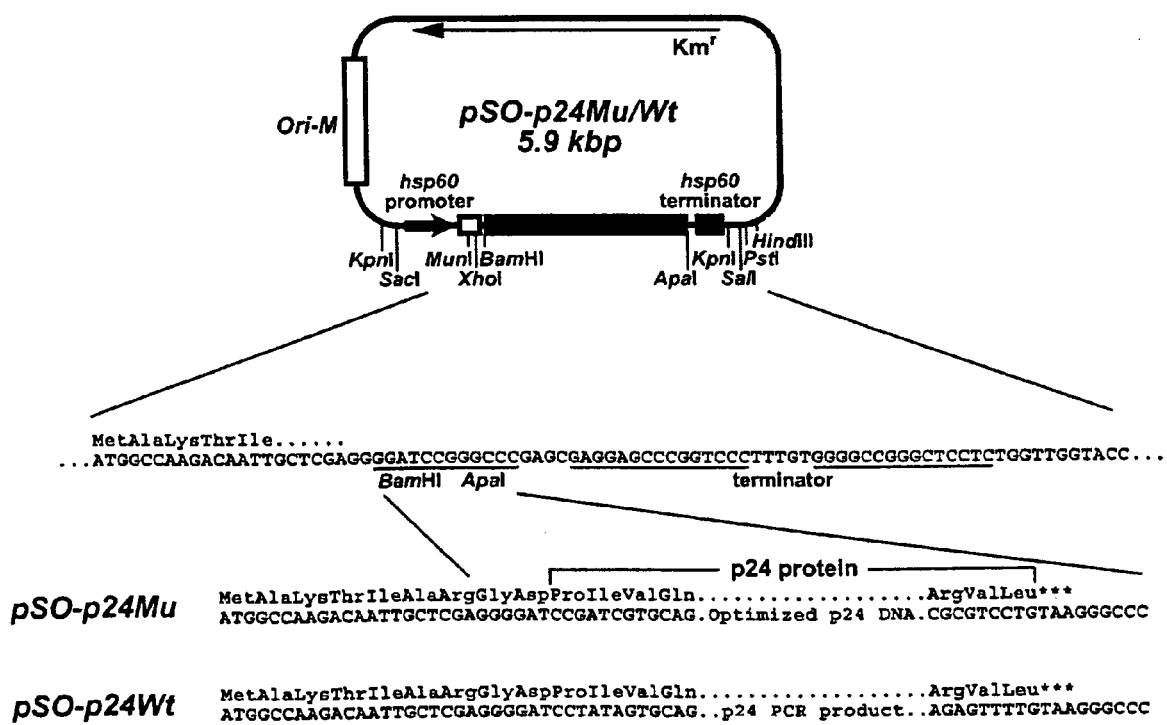

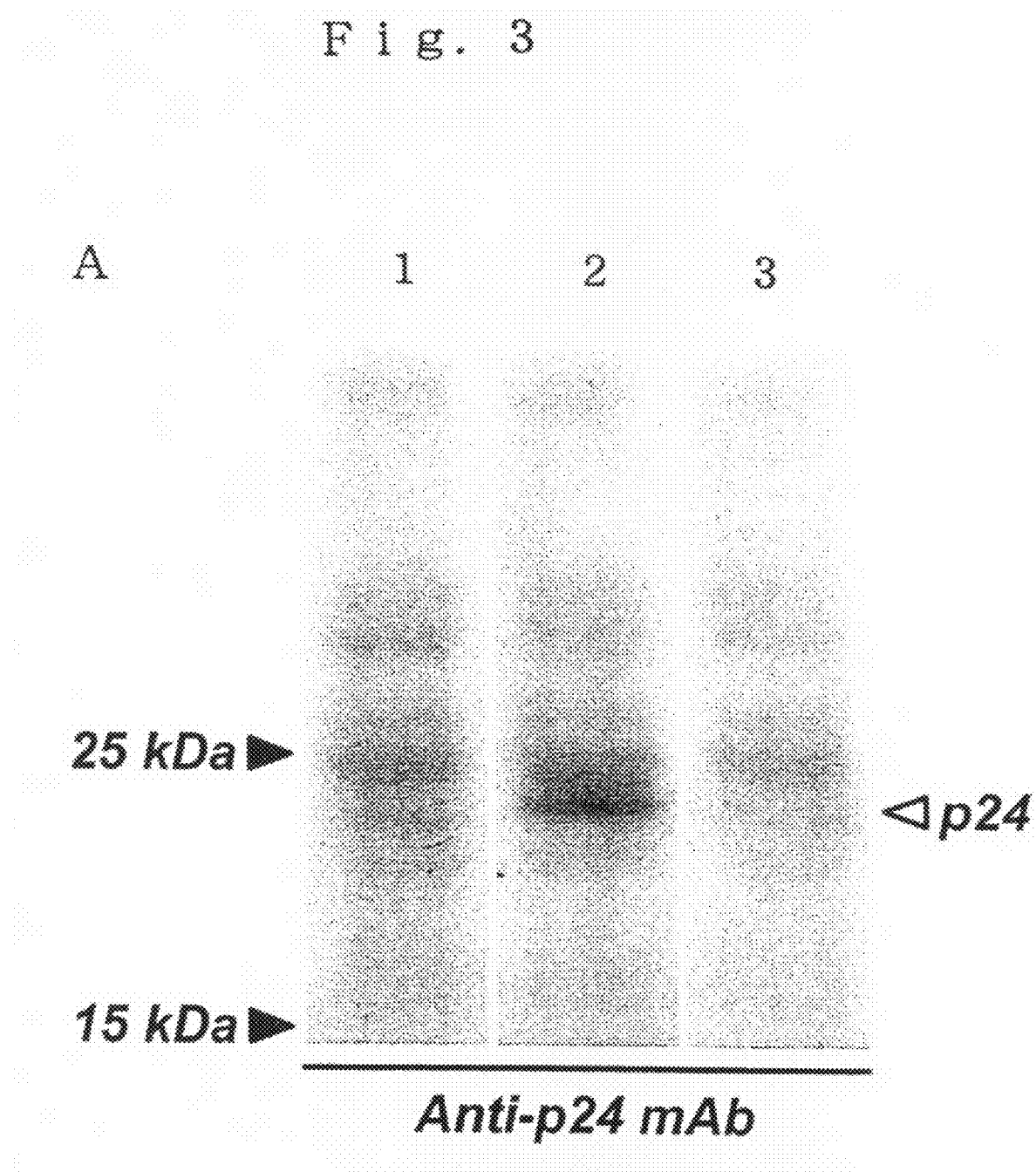

Fig. 3/1
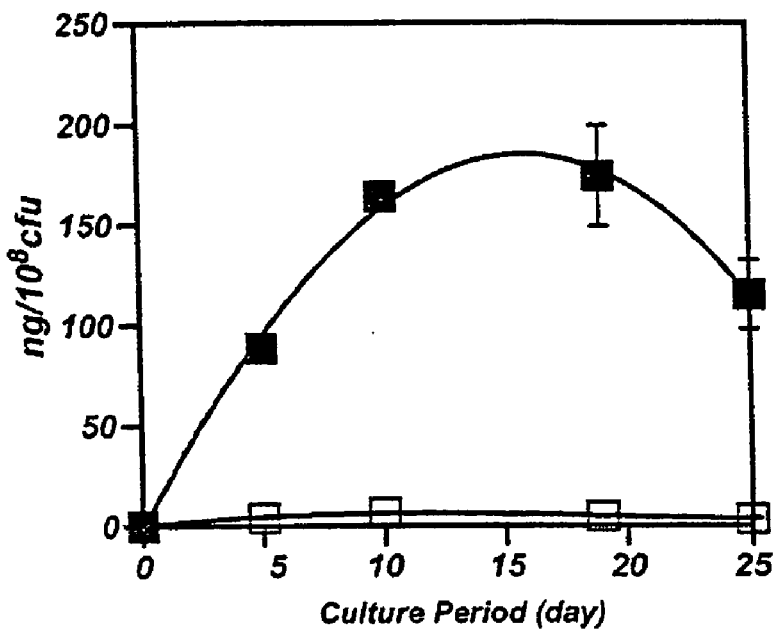
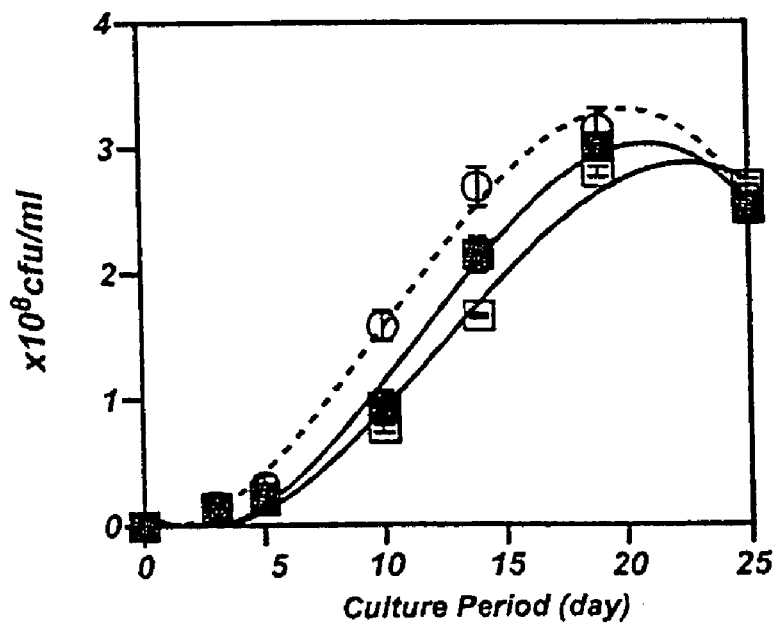

Fig. 4
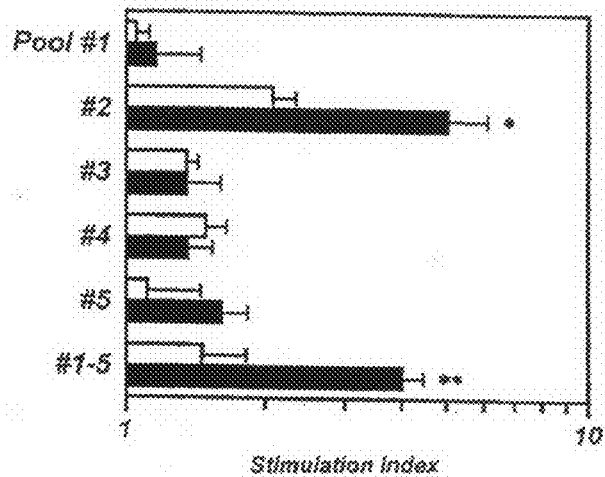
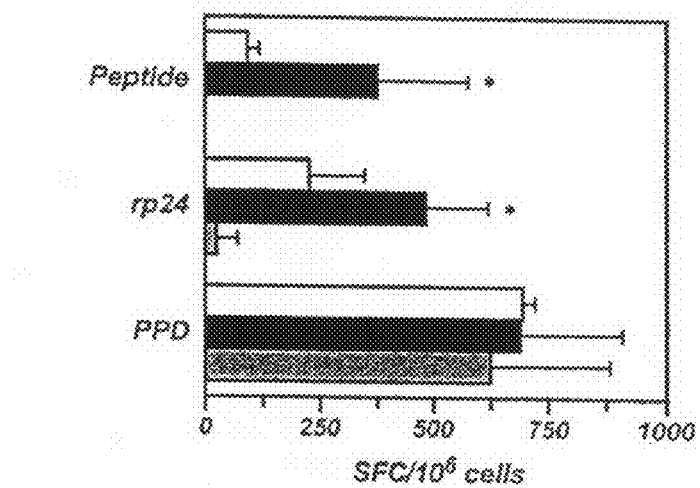
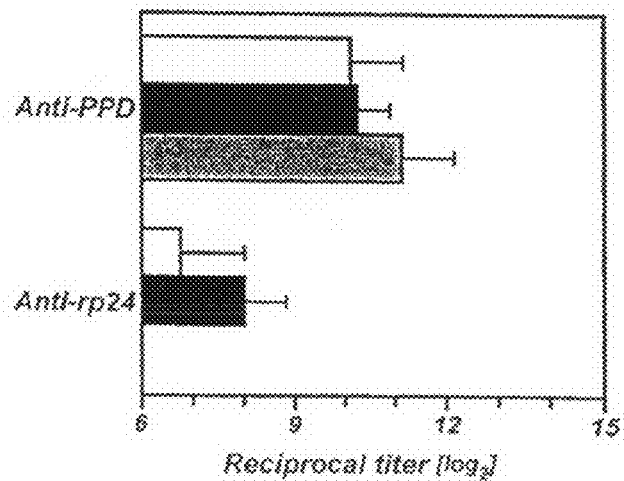

SEQUENCE LISTING

```
<160> NUMBER OF SEQ ID NOS: 13

<210> SEQ ID NO 1
<211> LENGTH: 25
<212> TYPE: DNA
<213> ORGANISM: Artificial Sequence
<220> FEATURE:
<223> OTHER INFORMATION: Description of artificial Sequence: Synthetic
      oligonucleotide

<400> SEQUENCE: 1
aatggatcct atagtgcaga acctc                                          25

<210> SEQ ID NO 2
<211> LENGTH: 31
<212> TYPE: DNA
<213> ORGANISM: Artificial Sequence
<220> FEATURE:
<223> OTHER INFORMATION: Description of artificial Sequence: Synthetic
      oligonucleotide

<400> SEQUENCE: 2
aatgggccct tacaaaactc ttgctttatg g                                   31

<210> SEQ ID NO 3
<211> LENGTH: 706
<212> TYPE: DNA
<213> ORGANISM: Artificial Sequence
<220> FEATURE:
<221> NAME/KEY: CDS
<222> LOCATION: (5)..(700)
<220> FEATURE:
<223> OTHER INFORMATION: Description of Artificial Sequence: Synthetic
      polynucleotide

<400> SEQUENCE: 3 ggat ccg atc gtc cag aac ctg cag ggc cag atg gtc cac cag gcc atc    49
     Pro Ile Val Gln Asn Leu Gln Gly Gln Met Val His Gln Ala Ile
       1               5                  10                  15
```

```
tcg ccg cgc acc ctg aac gcc tgg gtc aag gtc gtc gag gag aag gcc    97
Ser Pro Arg Thr Leu Asn Ala Trp Val Lys Val Val Glu Glu Lys Ala
             20                  25                  30 ttc tcg ccg gag gtc atc ccg atg ttc tcg gcc ctg tcg gag ggc gcc   145
Phe Ser Pro Glu Val Ile Pro Met Phe Ser Ala Leu Ser Glu Gly Ala
         35                  40                  45 acc ccg cag gac ctg aac acc atg ctg aac acc gtc ggc ggc cac cag   193
Thr Pro Gln Asp Leu Asn Thr Met Leu Asn Thr Val Gly Gly His Gln
     50                  55                  60 gcc gcc atg cag atg ctg aag gag acc atc aac gag gag gcc gcc gag   241
Ala Ala Met Gln Met Leu Lys Glu Thr Ile Asn Glu Glu Ala Ala Glu
 65                  70                  75 tgg gac cgc ctg cac ccg gtc cac gcc ggc ccc atc gca ccg ggc cag   289
Trp Asp Arg Leu His Pro Val His Ala Gly Pro Ile Ala Pro Gly Gln
 80                  85                  90                  95 atg cgc gag cct cgc ggc tcg gac atc gcc ggc acc acc tcg acc ctc   337
Met Arg Glu Pro Arg Gly Ser Asp Ile Ala Gly Thr Thr Ser Thr Leu
                100                 105                 110 cag gag cag atc ggc tgg atg acc cac aac ccg ccg atc ccg gtc ggc   385
Gln Glu Gln Ile Gly Trp Met Thr His Asn Pro Pro Ile Pro Val Gly
            115                 120                 125 gag atc tac aag cgc tgg atc atc ctg ggc ctg aac aag atc gtc cgc   433
Glu Ile Tyr Lys Arg Trp Ile Ile Leu Gly Leu Asn Lys Ile Val Arg
        130                 135                 140 atg tac tcg ccg acc tcg atc ctg gac atc cgc cag ggt ccg aag gag   481
Met Tyr Ser Pro Thr Ser Ile Leu Asp Ile Arg Gln Gly Pro Lys Glu
        145                 150                 155 ccg ttc cgc gac tac gtc gac cgc ttc tac aag acc ctc cgc gcc gag   529
Pro Phe Arg Asp Tyr Val Asp Arg Phe Tyr Lys Thr Leu Arg Ala Glu
160                 165                 170                 175 cag gcg tcg cag gag gtc aag aac tgg atg acc gag acc ctg ctg gtc   577
Gln Ala Ser Gln Glu Val Lys Asn Trp Met Thr Glu Thr Leu Leu Val
                180                 185                 190 cag aac gcc aac ccg gac tgc aag acc atc ctg aag gcc ctg ggt ccg   625
Gln Asn Ala Asn Pro Asp Cys Lys Thr Ile Leu Lys Ala Leu Gly Pro
            195                 200                 205 ggc gcc acc ctg gag gag atg atg acc gcc tgc cag ggc gtc ggc ggc   673
Gly Ala Thr Leu Glu Glu Met Met Thr Ala Cys Gln Gly Val Gly Gly
        210                 215                 220 ccg ggc cac aag gcg cgc gtc ctg taa gggccc                        706
Pro Gly His Lys Ala Arg Val Leu
        225                 230

<210> SEQ ID NO 4
<211> LENGTH: 15
<212> TYPE: PRT
<213> ORGANISM: Artificial Sequence
<220> FEATURE:
<223> OTHER INFORMATION: Description of artificial Sequence: Synthetic
      oligopeptide

<400> SEQUENCE: 4

Leu Glu Arg Phe Ala Val Asn Pro Gly Leu Leu Glu Thr Ser Glu
 1               5                  10                  15

<210> SEQ ID NO 5
<211> LENGTH: 15
<212> TYPE: PRT
<213> ORGANISM: Artificial Sequence
<220> FEATURE:
<223> OTHER INFORMATION: Description of artificial Sequence: Synthetic
      oligopeptide
```

<400> SEQUENCE: 5

Asn Ile Gln Gly Gln Met Val His Gln Ala Ile Ser Pro Arg Thr
 1               5                  10                  15

<210> SEQ ID NO 6
<211> LENGTH: 5
<212> TYPE: PRT
<213> ORGANISM: Artificial Sequence
<220> FEATURE:
<223> OTHER INFORMATION: Description of artificial Sequence: Synthetic
      oligopeptide

<400> SEQUENCE: 6

Met Ala Lys Thr Ile
 1               5

<210> SEQ ID NO 7
<211> LENGTH: 13
<212> TYPE: PRT
<213> ORGANISM: Artificial Sequence
<220> FEATURE:
<223> OTHER INFORMATION: Description of artificial Sequence: Synthetic
      oligopeptide

<400> SEQUENCE: 7

Met Ala Lys Thr Ile Ala Arg Gly Asp Pro Ile Val Gln
 1               5                  10

<210> SEQ ID NO 8
<211> LENGTH: 85
<212> TYPE: DNA
<213> ORGANISM: Artificial Sequence
<220> FEATURE:
<223> OTHER INFORMATION: Description of artificial Sequence: Synthetic
      oligonucleotide

<400> SEQUENCE: 8
atggccaaga caattgctcg aggggatccg ggcccgagcg aggagcccgg tccctttgtg      60
gggccgggct cctctggttg gtacc                                            85

<210> SEQ ID NO 9
<211> LENGTH: 39
<212> TYPE: DNA
<213> ORGANISM: Artificial Sequence
<220> FEATURE:
<223> OTHER INFORMATION: Description of artificial Sequence: Synthetic
      oligonucleotide

<400> SEQUENCE: 9
atggccaaga caattgctcg aggggatccg atcgtgcag                             39

<210> SEQ ID NO 10
<211> LENGTH: 39
<212> TYPE: DNA
<213> ORGANISM: Artificial Sequence
<220> FEATURE:
<223> OTHER INFORMATION: Description of artificial Sequence: Synthetic
      oligonucleotide

<400> SEQUENCE: 10
atggccaaga caattgctcg aggggatcct atagtgcag                             39

<210> SEQ ID NO 11
<211> LENGTH: 18
<212> TYPE: DNA

-continued

<213> ORGANISM: Artificial Sequence
<220> FEATURE:
<223> OTHER INFORMATION: Description of artificial Sequence: Synthetic
      oligonucleotide

<400> SEQUENCE: 11
cgcgtcctgt aagggccc                                                          18

<210> SEQ ID NO 12
<211> LENGTH: 18
<212> TYPE: DNA
<213> ORGANISM: Artificial Sequence
<220> FEATURE:
<223> OTHER INFORMATION: Description of artificial Sequence: Synthetic
      oligonucleotide

<400> SEQUENCE: 12
agagttttgt aagggccc                                                          18

<210> SEQ ID NO 13
<211> LENGTH: 706
<212> TYPE: DNA
<213> ORGANISM: Artificial Sequence
<220> FEATURE:
<221> NAME/KEY: CDS
<222> LOCATION: (5)..(700)
<220> FEATURE:
<223> OTHER INFORMATION: Description of Artificial Sequence: Synthetic
      polynucleotide

<400> SEQUENCE: 13

```
ggat cct ata gtg cag aac ctc cag ggg caa atg gta cat cag gcc ata        49
     Pro Ile Val Gln Asn Leu Gln Gly Gln Met Val His Gln Ala Ile
       1               5                  10                  15 tca cct aga act tta aat gac tgg gta aaa gta gta gaa gag aag gtt        97
Ser Pro Arg Thr Leu Asn Ala Trp Val Lys Val Val Glu Glu Lys Ala
            20                  25                  30 ttc agc cca gaa gta ata ccc atg ttt tca gca tta tca gaa gga gcc       145
Phe Ser Pro Glu Val Ile Pro Met Phe Ser Ala Leu Ser Glu Gly Ala
        35                  40                  45 acc cca caa gat tta aat acc atg cta aac aca gtg ggg gga cat caa       193
Thr Pro Gln Asp Leu Asn Thr Met Leu Asn Thr Val Gly Gly His Gln
    50                  55                  60 gca gcc atg caa atg tta aaa gag acc atc aat gag gaa gct gca gaa       241
Ala Ala Met Gln Met Leu Lys Glu Thr Ile Asn Glu Glu Ala Ala Glu
65                  70                  75 tgg gat aga ttg cat cca gtg cat gca ggg cct att gca cca ggc cag       289
Trp Asp Arg Leu His Pro Val His Ala Gly Pro Ile Ala Pro Gly Gln
 80                  85                  90                  95 atg aga gaa cca agg gga agt gac ata gca gga act act agt acc ctt       337
Met Arg Glu Pro Arg Gly Ser Asp Ile Ala Gly Thr Thr Ser Thr Leu
                100                 105                 110 cag gaa caa ata gga tgg atg aca cat aat cca cct atc cca gta gga       385
Gln Glu Gln Ile Gly Trp Met Thr His Asn Pro Pro Ile Pro Val Gly
            115                 120                 125 gaa atc tat aaa aga tgg ata atc ctg gga tta aat aaa ata gta aga       433
Glu Ile Tyr Lys Arg Trp Ile Ile Leu Gly Leu Asn Lys Ile Val Arg
        130                 135                 140 atg tat agc cct acc agc att ctg gac ata aga caa gga cca aag gaa       481
Met Tyr Ser Pro Thr Ser Ile Leu Asp Ile Arg Gln Gly Pro Lys Glu
    145                 150                 155 ccc ttt aga gac tat gta gac cga ttc tat aaa act cta aga gcc gag       529
Pro Phe Arg Asp Tyr Val Asp Arg Phe Tyr Lys Thr Leu Arg Ala Glu
160                 165                 170                 175
```

```
caa gct tca caa gag gta aaa aat tgg atg aca gaa acc ttg ttg gtc    577
Gln Ala Ser Gln Glu Val Lys Asn Trp Met Thr Glu Thr Leu Leu Val
            180                 185                 190 caa aat gcg aac cca gat tgt aag act att tta aaa gca ttg gga cca    625
Gln Asn Ala Asn Pro Asp Cys Lys Thr Ile Leu Lys Ala Leu Gly Pro
            195                 200                 205 gga gcg aca cta gaa gaa atg atg aca gca tgt cag gga gtg ggg gga    673
Gly Ala Thr Leu Glu Glu Met Met Thr Ala Cys Gln Gly Val Gly Gly
            210                 215                 220 ccc ggc cat aaa gca aga gtt ttg taa gggccc                         706
Pro Gly His Lys Ala Arg Val Leu
            225                 230
```

RECOMBINANT BCG VACCINE

This application is a divisional of Ser. No. 10/524,586, filed Mar. 31, 2005, which is a 371 U.S. national stage of International Application No. PCT/JP03/10303 filed Aug. 13, 2003.

TECHNICAL FIELD

The present invention relates to a recombinant BCG vaccine. More particularly, the present invention relates to a recombinant BCG vaccine capable of inducing a sufficient immune response against a foreign antigen protein at low doses.

BACKGROUND ART

A bovine tubercle bacillus attenuated BCG strain (*Mycobacterium bovis* BCG, hereinafter referred to as "BCG") has been known as the most common live bacteria vaccine because of its safety.

On the other hand, as gene recombinant technologies have been keenly developed and improved for the past ten plus years, there have been many studies for modifying microorganisms such as viruses and bacteria to produce a foreign antigen protein and using them as vaccine vectors for preventing and treating various kinds of infectious diseases and cancers. Regarding BCG, for example, recombinant BCG vaccines targeted to human immunodeficiency virus (HIV) and simian immunodeficiency virus (SIV) have been also reported (J. Immunol. 164: 4968-4978, 2000, J. Virol. 71: 2303-2309, 1997, and Infect Immun. 57: 283-288, 1989).

The BCG strain is considered as a candidate for providing an excellent recombinant vaccine because of its safety and easy supply. However, the conventional recombinant BCG vaccine has not always been sufficient in its capability of inducing immunity to infection, cancer, or the like to be provided as a target. For example, in the case of immunizing a guinea pig with a recombinant BCG vaccine targeted at HIV-1, it should be dosed 10 to 100 times higher than a typical dosage (0.05 to 0.1 mg) of BCG vaccine generally used for human (Proc. Natl. Acad. Sci. USA. 92: 10698-10697, 1995).

On the other hand, in the recombinant vaccine, as means for providing a foreign antigen with high immunogenicity, the optimization of codon is attempted. Those are, the codon optimizations, such as listeriolysin O of *Listeria monocytogenes* (J. immunol 161: 5594-5599, 1998), HIV-1 Gag (J. Virol. 75: 10991-11001, 200; J. Virol. 74: 2628-2635, 2000), Env (J. Virol. 72: 1497-1503, 1998), tetanus toxin (Vaccine 19: 810-815, 2000), L1 protein of human papilloma virus (J. Virol. 75: 9201-9209, 2001), merozoite surface protein 1 of falciparum malaria protozoan (*Plasmodium falciparum*) (Infect. Immun. 69: 7250-7253, 2001). However, these codon optimizations are those obtained by humanized codons for each amino acid of antigens. In addition, those recombinant vaccines are also DNA vaccines (naked DNA), so that there is no report at all about effects of the codon optimization in vaccine predominantly composed of other recombinant vector of BCG strain or the like.

The invention of the present application has performed in consideration of circumstances described above, and addresses to provide a recombinant BCG vaccine which is excellent in the expression amount of an antigenic protein and, as a consequence, capable of inducing a sufficient immune response to the target infectious disease, cancer, or the like even though the dosage thereof is almost equal to that of typical BCG vaccine.

DISCLOSURE OF THE INVENTION

As an invention to solve the above problem, the invention of the present application is to provide a recombinant BCG vaccine being transformed with an expression vector that has a polynucleotide encoding a foreign antigenic protein, wherein the polynucleotide is a modified one in which the third position of each codon is substituted with G or C without a change of an amino acid.

In this recombinant BCG vaccine, as one of preferred modes, the triplets of each codon in the modified polynucleotide are substituted so as to include G and C as much as possible without a change in type of an amino acid.

In this invention, the term "polypeptide" means a molecule constructed of phosphoric esters of the respective nucleosides (ATP, GTP, CTP, UTP; or dATP, dGTP, dCTP, dTTP) being bonded together, in which purine or pyrimidine is in β-N-glycoside linkage with a sugar. In addition, the term "protein" or "peptide" means a molecule constructed of a plurality of amino acid residues bonded with each other through amide bonds (peptide bonds).

Other terms and concepts in the present invention will be defined concretely in the description of embodiments and examples of the invention. In addition, various kinds of techniques to be used for carrying out the invention can be easily and reliably conducted by a person skilled in the art in accordance with known publications or the like, except for particular techniques cited the sources thereof. For instance, genetic engineering and molecular biological techniques are described in Sambrook and Maniatis, in Molecular Cloning—A Laboratory Manual, Cold Spring Harbor Laboratory Press, New York, 1989; Ausubel, F. M. et al., Current Protocols in Molecular Biology, John Wiley & Sons, New York, N.Y., 1995, and so on.

BRIEF DESCRIPTION OF DRAWINGS

FIG. 1 shows nucleotide sequences and deduced amino acid sequence alignments of p24 gene from pNL4-3 and synthetic p24 gene with mycobacterial optimal codons (optimized). For cloning to pUC-hspK vector, the BamHI and ApaI restriction sites were attached at both 5'- and 3'-terminus of each DNA fragments. Asterisks indicated identical sequences to pNL4-3 p24 gene. Ter termination codon. The DNA sequence in FIG. 1 corresponds to SEQ ID NO:13.

FIG. 2 shows structure of expression vectors pSO-p24Mu and -p24Wt. (A) Schematic representation of expression units of HIV-1 p24. Each arrow and solid square exhibits transcriptional direction of hsp60 promoter and terminator. Grey, solid and open bars show DNA fragment of mycobacteria, synthetic p24 gene, and PCR fragment of p24 gene, respectively. (B) Details of expression vectors pSO-p24Mu and -p24Wt. Ori-M and Km$^r$ indicate mycobacterial replication origin and kanamycin resistance genes, respectively. In FIG. 2B, the first depicted amino acid sequence from the top, which is above the DNA sequence showing BamHI and ApaI restriction sites, corresponds to SEQ ID NO: 6. In FIG. 2B, the second and third depicted amino acid sequences from the top, which are also listed in the pSO-p24Wt, correspond to SEQ ID NO:7. In FIG. 2B, the first depicted DNA sequence from the upper left, which shows BamHI and ApaI restriction sites, corresponds to SEQ ID NO:8. In FIG. 2B, the second depicted DNA sequence from the upper left corresponds to SEQ ID NO:9. In FIG. 2B, the third DNA sequence on the left hand side corresponds to SEQ ID NO:10. In FIG. 2B, the first DNA sequence on the lower right side corresponds to SEQ ID NO:11. In FIG. 2B, the second DNA sequence on the lower right side corresponds to SEQ ID NO:12.

FIG. 3 shows comparison of p24 expression level and growth rate between rBCG-p24Mu and -p24Wt. (A) Anti-p24 monoclonal antibody (V107) reactive proteins were visualized by western blot. Lanes: 1, lysate of rBCG-p24Wt; 2, lysate of rBCG-p24Mu; 3, lysate of harboring pSO246 (negative control). (B) Comparison of p24 concentration in whole cell lysates of rBCG-p24Mu and -p24Wt. rBCG cells were harvested from one ml of each culture periodically, sonicated and applied to commercial p24 antigen EIA. Solid and open squares were indicated rBCG-p24Mu and -p24Wt respectively. The data were represented as mean±s.d. of different clones. (C) Kinetics of growth rates in recombinant clones. One ml of each culture was collected periodically, measured O.D. at 470 nm and calculated cell densities from the absorbance, described below; Density (μg/ml)=Absorbance at 470 nm×1412.3+73.063. The cfu were translated from densities, and plotted. Solid square, open square, and open circle were indicated rBCG-p24Mu, -p24Wt, and -pSO246, respectively. The data were represented as mean±s.d. of different clones.

FIG. 4 shows cellular and humoral immune responses in mice immunized with rBCGs. (A) Lymphocyte proliferation against Gag p24 overlapping peptides. The proliferative activity was showed by stimulation index (SI). Solid and open columns indicate SI values of rBCG-p24Mu and -p24Wt-immunized mice. The data were represented as mean SI+s.d. of groups of mice. Asterisks indicated statistical significance (*, $p<0.02$; **, $p<0.002$). (B) Determination of antigen-specific IFN-γ secreting cells by ELISPOT assay. Solid, open, and gray columns indicate number of SFCs of rBCG-p24 Mu, -p24Wt, and -pSO246-immunized mice, respectively. The data were represented as mean number of SFCs/$10^6$ cells+s.d. of groups of mice. Asterisk indicated statistical significance (*, $p<0.05$ against rBCG-p24Wt-immunized mice). (q Anti-p24-specific and anti-PPD-specific IgG Abs in plasma of mice immunized with rBCGs. Solid, open, and gray columns indicate reciprocal $\log_2$ titer of rBCG-p24 Wt, -p24Mu, and -pSO246-immunized mice, respectively. The titers were determined by an endpoint ELISA. The data were represented as mean titer+s.d. of groups of mice.

BEST MODE FOR CARRYING OUT THE INVENTION

The recombinant BCG vaccine of this invention contains a recombinant BCG as an active ingredient, where the recombinant BCG is transformed with an expression vector that has a polynucleotide encoding a foreign antigenic protein. The polynucleotide encoding the foreign antigenic protein is characterized in that it is a modified polypeptide in which the third position of the codon encoding each of amino acid residues is substituted with G (guanine) or C (cytosine) under the conditions of which the amino acid residues in the amino acid sequence of the antigenic protein being coded are not changed.

The substitutions in the respective codons are shown in Table 1 in a concretive manner (the column of "optimal codon"). That is, for example, there are four codons for encoding glycine (Gly): GGT, GGC, GCA, and GGG. The Gly codon agreed with the above criteria is GGC or GGG. Therefore, the Gly codon in the amino acid sequence of some antigenic protein is GGT or GGA, the third T (thymine) or A (adenine) is substituted with C or G.

TABLE 1

| Amino acid | Codon | | Optimal codon |
|---|---|---|---|
| Glycine | Gly G | GGT, GGC, GGA, GGG | GGC, GGG |
| Alanine | Ala A | GCT, GCC, GCA, GCG | GCC, GCG |
| Valine | Val V | GTT, GTC, GTA, GTG | GTC, GTG |
| Leucine | Leu L | CTT, CTC, CTA, CTG, TTA, TTG | CTC, CTG, TTG |
| Isoleucine | Ile I | ATT, ATC, ATA | ATC |
| Serine | Ser S | TCT, TCC, TCA, TCG, AGT, AGC | TCC, TCG, AGC |
| Threonine | Thr T | ACT, ACC, ACA, ACG | ACC, ACG |
| Cystein | Cys C | TGT, TGC | TGC |
| Methionine | Met M | ATG | ATG |
| Asparagine | Asn N | AAT, AAC | AAC |
| Glutamine | Gln Q | CAA, CAG | CAG |
| Phenylalanine | Phe F | TTT, TTC | TTC |
| Tyrosine | Tyr Y | TAT, TAC | TAC |
| Tryptophan | Trp W | TGG | TGG |
| Aspartate | Asp D | GAT, GAC | GAC |
| Glutamate | Glu E | GAA, GAG | GAG |
| Histidine | His H | CAT, CAC | CAC |
| Lysine | Lys K | AAA, AAG | AAG |

TABLE 1-continued

| Amino acid | Codon | | Optimal codon |
|---|---|---|---|
| Arginine | Arg R | CGT, CGC, CGA, CGG, AGA, AGG | CGC, CGG, AGG |
| Proline | Pro P | CCT, CCC, CCA, CCG | CCC, CCG |

In this invention, a preferable mode is that all positions in each codon is substituted so as to include G or C as much as possible under the conditions in which the type of an amino acid residue encoded by such a codon is not changed. Such a kind of the substitution can be applied on leucine (Leu) and arginine (Arg). That is, among the optimal codons shown in Table 1, CTC or CTG is preferably selected as a Leu codon rather than the codon (TTG) containing two "T"s. In addition, CGC or CGG is preferably selected as an Arg codon rather than the codon (AGG) containing "A".

The codon substitution as described above is based on the following findings. That is, it is known that the BCG genome consists of DNA with a high G+C contents and the third position of the codon strongly prefers GC pair (J. Virol. 75: 9201-9209, 2001; Infect. Immun. 57: 283-288, 1989). Furthermore, from the accumulated information on BCG genes (Nucl. Acids Res. 28: 292, 2000), it is also known that the AGA codon for Arg and the TTA codon for Leu are less frequently used (0.9% and 1.6% of total codons, respectively). On the other hand, for instance, it is known that HIV-1 prefers an AT pair at the third position of the codon. In other words, in the coding sequence of the HIV-1 p24 gene, 9 out of 11 Arg codons use AGA and 6 out of 18 Leu codons use TTA. It is generally known that the preference of frequency in codon usage is correlated with the amount of corresponding aminoacyl tRNA in unicellular organisms (Nature 325: 728-730, 1987; Mol. Biol. Evol. 2: 13-34, 1985). It is considered that the amount of the aminoacyl tRNA for the Arg codon (AGA) and the Leu codon (TTA), which are preferred for the HIV-1 p24 gene, would be quite low in the BCG cell.

Accordingly, the present invention is designed to substitute a foreign antigenic polypeptide so as to become a base sequence agreed with the frequency of codon usage particularly preferable for the BCG cell (i.e., the third position of the codon is G or C, and furthermore the codon contains G or C as much as possible).

For introducing a preferable base substitution corresponding to each codon into the polynucleotide, the well-known Kunkel method (Proc. Natl. Acad. Sci. USA 82: 488, 1985 and Methods in Enzymology 154: 367, 1987), well-known methods such as one using a mutation kit, a mutation-inducing type PCR method, and so on may be applied.

For the BCG strain, one well-known in the art used in a vaccination against tuberculosis can be targeted. In addition, the expression vector to be introduced into the BCG strain may be one used for the conventional preparation of recombinant BCG vaccine, such as a BCG vector (e.g., plasmid pSO246). An expression vector can be constructed by inserting a polynucleotide that encodes any foreign antigenic protein (i.e., other than BCG) into a cloning site of this vector. Furthermore, in the following description, the foreign antigenic protein may be described as a "foreign polypeptide", the polypeptide that encodes such a foreign protein may be described as "foreign polynucleotides". Furthermore, the foreign polypeptide may be designed so as to be connected with any promoter and terminator sequences derived from the BCG strain (e.g., promotor and terminator sequence of heat shock protein derived from the BCG strain) to favorably express the foreign polypeptide.

The foreign polynucleotide is a polynucleotide (e.g., cDNA fragment) that encodes an antigenic protein, except for the BCG strain. The foreign polypeptide may be any of those capable of inducing an antigen-antibody reaction in vitro. Concretely, the targets may include a gag precursor p55 or p24 protein, an env protein gp120 or gp 160, a pol precursor protein, an nef protein, and a tat protein of the human immunodeficiency virus (HIV) which is a causative virus of the acquired immunodeficiency syndrome (AIDS). In addition, it may be also used in a similar antigenic polypeptide derived from the simian immunodeficiency virus (SIV). Alternatively, polypeptides that encode antigenic proteins of other pathogens (other pathogenic viruses and bacteria), or tumor cells may be used.

As a method of preparing a foreign polynucleotide, a polynucleotide, which is a substantial sequence of a cloned plasmid in which a genomic gene or a cDNA thereof that encodes a foreign polypeptide, may be cut off from such a cloned plasmid by means of an appropriate enzyme, or it may be obtained by means of amplification with the polymerase chain reaction (PCR) using a primer having an appropriate sequence. If it is not cloned, in the case of virus, bacterial or animal genomic DNA having the gene can be obtained by amplifying a DNA fragment by the above PCR using DNA or RNA as a template, which is originated from an animal cell infected with the virus.

The expression vector constructed as described above is introduced into the BCG strain by a well-known method such as a calcium chloride method or an electroporation, and then the expression of a foreign polypeptide from a transformed bacterium is confirmed by the western blotting or a well-known immunoassay (e.g., ELISA) to prepare the recombinant BCG of the present invention.

The recombinant BCG constructed as described above is suspended in a liquid carrier just as in the case of the typical BCG vaccine to prepare the recombinant BCG vaccine.

EXAMPLES

Hereinafter, the invention of the present application will be described in more detail and concretely by representing examples thereof. However, this application is not limited by the following examples.

1. Materials and Methods 1.1. Reagent

All enzymes and *Escherichia coli* HB101 competent cell for recombinant DNA procedure were purchased from Takara Bio Inc. (Tokyo, Japan). Primers for wild-type p24 gene amplification were from ESPEC Oligo Service Co. Ltd. (Tsukuba, Japan). Anti-HIV-1 Gag p24 monoclonal antibody, V107 was kindly provided by Dr. Ikuta, Osaka University, Osaka, Japan. Alkaline phosphatase-conjugated anti-mouse IgG for western immunoblot assay was purchased from New England Biolabs, Inc. (Beverly, Mass.).

1.2. Construction of HIV Antigen-Expression Vector and Transformation of BCG Gene manipulation was done using *E. coli* HB101 competent cell. Mycobacterial strain used in this study was BCG-Tokyo vaccine strain. Culture media for rBCG were Middlebrook 7H9 broth containing albumin dextrose complex (7H9-ADC; BBL Microbiology Systems, Cockeyville, Md.). A DNA fragment encoding hsp60 gene of BCG (Infect. Immun. 55:1466-75, 1987) was cloned into SmaI-SalI sites of pUC18 (pUC-hsp60). A synthetic DNA fragment which corresponds to multi-cloning site and terminator region of hsp60 gene was cloned into MunI-KpnI sites of pUC-hsp60 and then inserted KpnI linker at EcoRI site giving rise to pUC-hspK vector. The gag p24 gene of subtype B virus was amplified by PCR from pNL4-3 plasmid (J. Virol. 59:284-291, 1986) by using primers as follows: AATGGATCCTATAGTGCAGAACCTC (SEQ ID No. 1; forward, with underlined BamHI site) and AATGGGCCCTTACAAAACTCTTGCTTTATGG (SEQ ID No. 2; reverse, with underlined ApaI site). The PCR product was cloned to BamHI-ApaI sites of pUC-hspK in frame (pUC-hspK-p24Wt).

Figure 1:
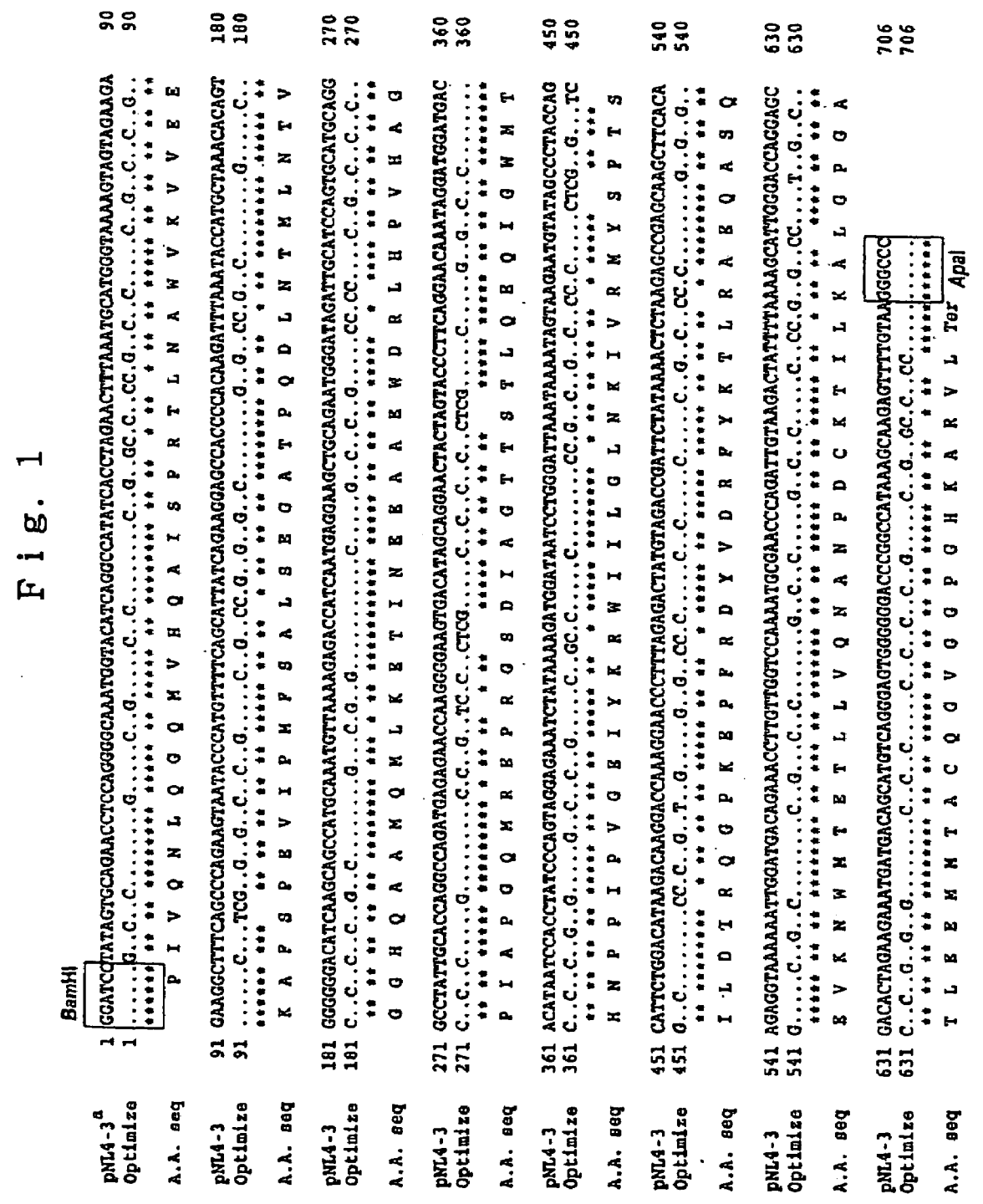

On the other hand, the whole p24 gene was chemically synthesized with preferable codons in BCG (SEQ ID No. 3) and then cloned to the same sites of pUC-hspK vector (pUC-hspK-p24Mu). Alignment of wild-type p24 sequence from pNL4-3 and synthesized p24 sequence are shown in FIG. 1. These vectors were digested with KpnI and a small fragment containing p24 expression unit named hsp-p24Wt and hsp-p24Mu (FIG. 2 A), were subcloned into a KpnI site of the stable *E. coli*-mycobacteria shuttle vector pSO246 (FEMS Microbiol. Lett. 135:237-243, 1996). Resulting plasmids were named pSO-p24Wt and -p24Mu, respectively. Schematic outline of expression vector construction is shown in FIG. 2 B. These plasmids and pSO246 were transformed into BCG using Gene-Pulser (Bio-Rad Laboratories Inc., Hercules, Calif.) according to Proc. Natl. Acad. Sci. USA 85:6987-6991, 1988 and transformants were selected on Middlebrook 7H10 agar supplemented with OADC enrichment (BBL Microbiology Systems) plate containing 20 µg/ml of kanamycin. The resulting recombinant clones harboring pSO-p24Wt, -p24Mu and pSO246 were designated as rBCG-p24Wt, -p24Mu and -pSO246 respectively.

1.3. Western Blot Analysis

Transformants of rBCGs were grown in 7H9-ADC broth for 2 weeks. A portion of culture media were collected, sonicated and applied to sodium dodecyl sulphate-polyacrylamide gel electrophoresis using Multi Gel 4/20 (Daiichi Pure Chemical Co. Ltd., Tokyo, Japan). Fractionated proteins were electroblotted onto a nitrocellulose membrane filter (Bio-Rad Laboratories Inc.), reacted with V107 monoclonal antibody (J. Gen. Virol. 73:2445-2450, 1992), and then probed with anti-mouse IgG conjugated with alkaline phosphatase and developed NBT (nitro blue tetrazolium chloride)/BCIP (5-bromo-4-chloro-3-indolyl phosphate, toluidine salt) substrate (Roche Diagnostics GmbH, Penzberg, Germany).

1.4. Detection of Gag p24 Antigen in rBCGs

Transformants of rBCGs were grown in 7H9-ADC broth. A portion of culture media were periodically collected and sonicated. P24 antigen concentration in cell extract was determined by commercial antigen EIA (HIVAG-1MC, Abbott Laboratories, Abbott Park, Ill.). Expression of HIV Gag p24 protein was represented as p24 protein concentrations (ng) per $10^8$ colony-forming units (cfu) of bacilli.

1.5. Delayed-Type Hypersensitivity (DTH) Reaction in Guinea Pig

Hartley strain female guinea pigs (body weight: ca. 350 g) were immunized with 0.1 0.5 5 mg of rBCG subcutaneously in 0.1 ml of saline) (n=3). To investigate DTH skin reactions, 0.1 µg of the purified protein derivative of tuberculin (PPD), 10 µg or 1 µg of the recombinant $HIV_{IIIB}$ Gag p24 protein (rp24; Immuno Diagnostics, Inc. Woburn, Mass.) per 100 µl of saline were injected intradermally into the rBCG-immunized guinea pigs, respectively. Saline was used for the negative control. After 24 hours, skin reactions were measured.

1.6. Mice and Immunization

Female BALB/c ($H-2^d$) mice, 6-8 weeks of age were purchased from Charles River Japan Inc. (Yokohama, Japan). Mice were acclimated to the experimental animal facility for more than 1 week before using experiment and maintained in the facility under pathogen-free conditions and were maintained according to the institutional animal care and use guidelines of the National Institute of Infectious Diseases (NIID), Japan. The study was conducted in a biosafety level 2 facility under the approval of an institutional committee for biosafety and in accordance with the requirements of the World Health Organization.

1.7. Preparation of Single-Cell Suspension

All mice were sacrificed at 10 weeks post inoculation (p.i.). Single-cells from spleen were isolated by gently testing the tissue through a cell strainer (Becton Dickinson, Franklin Lakes, N.J.). After hemolytication, the cells were resuspended in complete medium (CM; RPMI 1640 supplemented with 10% heat-inactivated FCS, $5.5 \times 10^{-5}$ M β-mercaptoethanol, 50 U/ml penicillin and 50 µg/ml streptomycin).

1.8. Lymphocyte Proliferation

Single-cell suspensions were adjusted to $2 \times 10^6$ cells/ml in CM. Equal volume of cells and CM or CM with HIV-HXB2 Gag overlapping peptide (NIH AIDS Research & Reference Reagent Program) at 50 µg/ml were mixed to give a final concentration of $1 \times 10^6$ cells/ml in media alone or media with peptide at 25 µg/ml. Used overlapping peptides were p11 (LERFAVNPGLLETSE; SEQ ID No. 4) through p35 (NIQGQMVHQAISPRT; SEQ ID No. 5) that covered Gag p24 region, pooled five peptides each or all of them for stimulation. Then cell suspension with or without the peptides were added to round-bottom 96-well plates (Corning Inc., Corning, N.Y.) in triplicate and incubated at 37° C., 5% $CO_2$ in air humidified environment for 48 h. The final 6 h before harvesting, 1.0 µCi of [$^3$H]Thymidine were added and harvested onto grass-fiber filters (GF/C; PerkinElmer Life Science Inc., Boston, Mass.), and wells were counted by liquid scintillation counter (TopCount; PerkinElmer Life Science Inc.).

1.9. ELISPOT Assay

HIV Gag p24- and PPD-specific IFN-γ secreting cells were assessed by Mouse IFN-γ Development Module and ELISpot Blue Color Module (R&D Systems Inc., Minneapolis, Minn.). Briefly, single-cell suspensions from spleen were cultured in CM with or without 25 µg/ml of pooled Gag overlapping peptide (p11-35), 5 µg/ml of rp24 or 2.5 µg/ml of tuberculin purified protein derivatives (PPD) for 48 h at 37° C., 5% $CO_2$ in air humidified environment. After incubation, cells were washed once with RPMI 1640 medium, and resuspended in CM. For detection, 96-well nitrocellulose plates (Millititer HA; Millipore Co., Bedford, Mass.) were coated with capture antibody at 4° C. overnight and washed with PBS. After blocking with CM for 3 h, 100 µl of pre-stimulated cells were added at varying concentrations into each well and incubated for 16 h at 37° C., 5% $CO_2$ in air humidified environment. Then plates were washed with PBS containing 0.05% Tween 20 (PBS-T) and incubated with detection antibody. After incubation overnight at 4° C., the plates were washed with PBS-T and incubated with alkaline phosphatase-conjugated streptavidin for 2 h at room temperature. After washing with PBS-T, the plates were developed at room temperature with NBT/BCIP substrate. Then plates were washed with water and dried, and then spot forming cells (SFCs) were quantified. Wells were imaged and SFCs were counted using the KS ELISPOT compact system (Carl Zeiss, Berlin, Germany). A SFC was defined as a dark blue spot with a fuzzy border (J. Virol. 76:875-884, 2002). To determine significant levels, a baseline for each stimulant was established using the average and standard deviation of the number of SFC for each stimulant. A threshold significance value corresponding to this average plus two standard deviations was then determined. A response was considered positive if the number of SFC exceeded the threshold significance level of the sample with no stimulant.

1.10. ELISA

Plasma was obtained by centrifugation of blood at 10,000 g for 5 minutes. All samples were store at 80° C. until use. PPD- and p24-specific IgG titers in plasma were determined by an endpoint ELISA. 96-well microtiter plates (MaxiSorp™; Nunc A/S, Roskilde, Denmark) were coated with 1 µg/ml of rp24 or PPD in carbonate-bicarbonate buffer (35 mM $NaHCO_3$, 15 mM $Na_2CO_3$, 0.02% $NaN_3$, pH9.6) and incubated at 4° C. overnight. The wells were blocked with PBS-1% BSA at 4° C. overnight and then plates were washed 3 times with PBS-T. The dilutions of plasma starting at $\frac{1}{2}^4$ were made with PBS-1% BSA, and duplicate diluents were then added at 100 µl/well into antigen-coated wells. After incubation at 4° C. overnight, the plates were washed and incubated with 1/2000 PBS-T dilution of horse radish peroxidase-conjugated goat anti-mouse IgG (H+L) (Southern Biotechnology Associates, Inc., Birmingham, Ala.). After 2 h incubation at 37° C., the plates were washed and developed at room temperature with tetramethyl-benzidine substrate (TMB+; DakoCytomation A/S, Copenhagen, Denmark) for 15 min in the dark. Then reactions were terminated by addition of 1 M HCl, 0.5 M $H_2SO_4$. Endpoint titers were expressed as the reciprocal $log_2$ of the highest dilution, which gave an optical density at 450 nm ($OD_{450}$) of $\geq 0.100$ OD unit above $OD_{450}$ of negative controls.

2. Results 2.1. Mycobacterial Codon-Optimization of HIV-1 Gene and Construction of Its Expression Vector The synthetic modified p24 gene was designed as shown in FIG. 1. The total G+C content of a coding region was 67.4%, which was higher than 43.4% of the wild-type p24 gene originated from pNL4-3. These two genes were cloned to the pUC-hspK vector (FIG. 2 A) and they were subcloned into pSO246 (FIG. 2 B). Each of the expression vectors was transformed into the BCG-Tokyo vaccine strain with the hsp60 promoter, and the rBCG-p24Mu with optimal codon usage of HIV gene and rBCG-p24Wt with wild-type codon usage were selected, respectively.

2.2. rBCG Significantly Enhances HIV Gene Expression by Insertion of Codon-Optimized HIV Gene In Vitro To compare the expression level of HIV-1 gag p24 gene between the two types of the BCG-HIV recombinants, we studied kinetics of both growth curve of the cultured rBCG cells and production ability of the HIV antigen by detecting p24 antigen protein (FIG. 3). At 2-wk culture periods, recombinant p24 protein in each of the lysates of rBCG-p24Mu and -p24Wt were detected to be a single band at the same approximately 24 kDa by Western blot analysis (FIG. 3 A). The p24 antigen expression level of rBCG-p24Mu was markedly elevated to be 175.0±25.1 ng/$10^8$ cfu of bacilli at more than 37.0-fold higher in rBCG-p24Mu than that (4.7±0.3 ng/$10^8$ pfu of bacilli) in rBCG-p24Wt (FIG. 3 B). Both rBCG-p24Wt and -p24Mu draws normal BCG growth curve compared with that of rBCG-pSO246 control transformant and peaked at 21 days of the cell culture (FIG. 3 C), suggested that the p24 antigen generation was correlated with the growth rate in the culture of rBCG-p24Mu. Thus, the BCG recombinant inserted with the codon-optimized HIV gag p24 gene was successfully generated to be capable of remarkably high expression at almost 200 ng of p24 antigen/$10^8$ cfu bacilli or 200 ng of p24 antigen/1 mg of bacilli.

2.3. DTH Reaction in Guinea Pig

To evaluate effect of improved p24 expression to immune responses, at first, the DTH skin reaction in guinea pig was tested. In a previous study (Proc. Natl. Sci. USA 92: 10693-10697, 1995), it was necessary to inject 5 mg for detecting a rBCG-V3J1 to detect V3 epitope-specific DTH reaction. However, as shown in Table 2, in the case of using rBCG-p24Mu that produces the improved p24, a remarkable DTH reaction against p24 was detected by 0.1 mg amount injection just as in the case of the injection of 5 mg rBCG-V3J1. By the way, any differential reactivity between rBCG-p24Mu-immunized and rBCG-p24Wt-immunized guinea pigs could not be observed.

TABLE 2

Sensitivity of HIV-1 Gag antigen-specific DHT induction in rBCG-p24-immunized guinea pig

| Immunization | Against PBS | Against PPD 0.1 µg | Against Gag antigen 1 µg | 10 µg |
|---|---|---|---|---|
| rBCG-p24 Wt 0.1 mg/s.c. | 0 | 15.0 | 0 | 10.0 |
| rBCG-p24 Mu 0.1 mg/s.c. | 0 | 14.5 | 0 | 10.0 |
| 5 mg/s.c. | 0 | 14.5 | 0 | 10.0 |
| rBCG-pSO246 0.1 mg/s.c. | 0 | 15.0 | 0 | 0 |

2.4. High Virus-Specific Immune Responses Were Elicited by Immunization with Low-Dose of the Codon-Optimized rBCG The possibility of the low-dose immunization of BCG recombinant with the codon-optimized gene expression was tested. Thirty BALB/c mice were divided into 3 groups of ten mice, and the animals in each group were immunized with rBCG-p24Mu, rBCG-p24Wt and rBCG-pSO246 at concentration of 0.01 and 0.1 mg of rBCG intradermally (i.d.) with 5 animals per each dose, respectively. Five more mice received saline alone and used as normal healthy control. At 10 weeks p.i., lymphocyte proliferation and IFN-γ ELISPOT cell generation in immunized animals were examined. Same study was repeated three times and all the three results were summarized.

In the lymphocyte proliferative response, significant activities (stimulation index was 5.04 and 4.02) were obtained with pooled peptides #2 (p16-20) and pooled total p24 peptides #1-5 (p11-35) in rBCG-p24Mu immunized mice. With 0.1 mg of the rBCG-p24Mu immunization, the lymphocyte proliferative responses to pool #2 and pool #1-5 increased to 10.08 and 8.05, respectively. In contrast, any significant virus-specific proliferation in 0.01 mg and 0.1 mg of rBCG-p24Wt immunized mice could not be detected (FIG. 4 A). These in vivo differences of proliferative responses between rBCG-p24Mu and -p24Wt were statistically significant comparing pool #2 and pool #1-5 (p=0.0102 and 0.0014) respectively. Any proliferation activities were not detected in rBCG-pSO246-immunized mice (data not shown).

In addition, p24-specific IFN-γ secreting cells were determined by ELISPOT assay. Both pooled p24 peptides (pool #1-5) and rp24-specific SFCs were detected in 0.1 mg of rBCG-p24Mu and -p24Wt-immunized mice, but not in similar dosage of rBCG-pSO246 immunized mice (FIG. 4 B). These responses from rBCG-p24Mu-immunized mice were $375\pm202$ SFC/$10^6$ splenocytes by stimulation with peptides and $483\pm138$ SFC/$10^6$ splenocytes by stimulation with rp24, that were much higher than those from rBCG-p24Wt did ($93\pm25$ and $227\pm120$ SFC/$10^6$ splenocytes, respectively). These differences between rBCG-p24Mu and -p24Wt were statistically significant comparing also peptides and rp24 (p=0.0327 and 0.0313) respectively. The PPD-specific SFCs were highly detected in all the mice tested ($670\pm180$ SFC/$10^6$ splenocytes).

Sera from all animals immunized with 0.1 mg of rBCG-p24Mu, rBCG-p24Wt and rBCG-pSO246 were assessed for HIV Gag p24 antigen-specific antibody generation at 10 weeks p.i. by endpoint antibody-ELISA against rp24 and PPD (FIG. 4 C). The antibodies against rp24 were generated generally low in animals immunized with the rBCG-p24Mu and -p24Wt: the anti-p24 antibody titer in sera of rBCG-p24Mu-immunized mice and rBCG-p24Wt were at titers of $2^8$ and $2^{6.75}$, respectively. Moreover, PPD-specific antibody titers were similarly detected in immunized animals around the titer of $2^{10}$. Thus, virus-specific cell-mediated immunity was significantly induced on the initial immune response, whereas its antibody response was low.

INDUSTRIAL APPLICABILITY

As described above in detail, the invention of this application provides a recombinant BCG vaccine having an excellent expression rate of antigen protein and, as a result, capable of inducing a sufficient immune response against target infectious disease, cancer, or the like at the same dose as that of the typical BCG vaccine.

The invention claimed is:

1. A method for producing a recombinant BCG for inducing an immune reaction against Human Immunodeficiency Virus (HIV) infection, which comprises;

modifying a polynucleotide encoding an antigenic Human Immunodeficiency Virus protein so that the third position of each codon is substituted with G or C without changing the amino acid encoded by the codon;

constructing an expression vector by inserting the modified polynucleotide into a vector; and transforming a BCG with the expression vector to produce a recombinant BCG for inducing an immune reaction against HIV infection.

2. The method according to claim 1, wherein the first and second position of each codon is further substituted with G or C without changing the amino acid encoded by the codon.

* * * * *